(12) United States Patent
Lefranc et al.

(10) Patent No.: US 8,933,290 B2
(45) Date of Patent: Jan. 13, 2015

(54) MESH IMPLANT

(75) Inventors: Olivier Lefranc, Chatillon sur Chalaronne (FR); Philippe Gravagna, Irigny (FR); Yves Bayon, Lyons (FR); Michel Therin, Lyons (FR)

(73) Assignee: Sofradim Production SAS (FR)

( * ) Notice: Subject to any disclaimer, the term of this patent is extended or adjusted under 35 U.S.C. 154(b) by 2170 days.

(21) Appl. No.: 11/821,987

(22) Filed: Jun. 26, 2007

(65) Prior Publication Data

US 2009/0005867 A1 Jan. 1, 2009

(51) Int. Cl.
| | | |
|---|---|---|
| A61F 13/00 | (2006.01) | |
| A61F 2/02 | (2006.01) | |
| A61F 2/00 | (2006.01) | |
| A61L 27/34 | (2006.01) | |
| A61L 27/54 | (2006.01) | |
| A61L 27/56 | (2006.01) | |
| A61L 31/10 | (2006.01) | |
| A61L 31/14 | (2006.01) | |
| A61L 31/16 | (2006.01) | |

(52) U.S. Cl.
CPC .............. *A61F 2/0063* (2013.01); *A61F 2/0045* (2013.01); *A61L 27/34* (2013.01); *A61L 27/54* (2013.01); *A61L 27/56* (2013.01); *A61L 31/10* (2013.01); *A61L 31/146* (2013.01); *A61L 31/16* (2013.01); *A61L 2300/606* (2013.01)
USPC .......................................... 602/49; 623/11.11

(58) Field of Classification Search
None
See application file for complete search history.

(56) References Cited

U.S. PATENT DOCUMENTS

| | | | |
|---|---|---|---|
| 5,217,493 | A | 6/1993 | Raad et al. |
| 5,428,022 | A | 6/1995 | Palefsky et al. |
| 5,667,839 | A | 9/1997 | Berg |
| 6,287,316 | B1 * | 9/2001 | Agarwal et al. ............... 606/151 |
| 6,408,656 | B1 | 6/2002 | Ory et al. |
| 6,413,742 | B1 | 7/2002 | Olsen et al. |
| 6,428,978 | B1 | 8/2002 | Olsen et al. |
| 6,478,727 | B2 | 11/2002 | Scetbon |
| 6,653,450 | B1 | 11/2003 | Berg et al. |
| 7,594,921 | B2 * | 9/2009 | Browning ..................... 606/151 |
| 2001/0003126 | A1 * | 6/2001 | Rhee et al. ................... 525/54.1 |
| 2004/0132365 | A1 | 7/2004 | Therin et al. |
| 2005/0021058 | A1 | 1/2005 | Negro |
| 2005/0085924 | A1 | 4/2005 | Darois et al. |
| 2005/0112349 | A1 * | 5/2005 | Laurencin et al. ......... 428/292.1 |
| 2007/0032805 | A1 | 2/2007 | Therin et al. |

FOREIGN PATENT DOCUMENTS

EP 1 273 312 1/2003

OTHER PUBLICATIONS

Pereira, M.S., et al., "Structure and Anticoagulant Activity of Sulfated Fucans", 1999, Journal of Biological Chemistry, 274, pp. 7656-7667.*

Nardella, A., et al., "Anticoagulant low molecular weight fucans . . . ", 1996, Carbohydrate Research, 289, 201-208.*
International Search Report from International Application No. PCT/IB2008/002695 dated Dec. 18, 2009.
Klinge U, et al. "Foreign body reaction to meshes used for the repair of abdominal wall hernias", *Eur J. Surg* 1999; 165:665-73.
S.B. Rao et al., "Use of Chitosan as a biomaterial: studies on its safety and haemostatic potential", *J. Biomed. Mater. Res.* 1997, 34:21-28.
Haroun-Bouhedja F,et al., "Relationship between sulfate groups and biological activities of fucans", *Thrombosis Res.* Dec 1, 2000 100(5):453-9.
Blondin C, et al., "Relationships between chemical characteristics and anticomplementary activity of fucans", *Biomaterials*. Mar. 1996; 17(6):597-603.
Kanabar V, et al., "Some structural determinants of the antiproliferative effect of heparin-like molecules on human airway smooth muscle", *Br J Pharmacol*. Oct. 2005; 146(3):370-7.
Strand SP et al., "Screening of chitosans and conditions for bacterial flocculation", *Biomacromolecules*, 2001, 2:126-133.
Varum KM et al., "In vitro degradation rates of partially N-acetylated chitosans in human serum", *Carbohydrate Research*, 1997, 299:99-101.
Amid PK., "Lichtenstein tension-free hernioplasty: Its inception, evolution, and principles", *Hernia* 2004; 8:1-7.
Welty G, et al., "Functional impairment and complaints following incisional hernia repair with different polypropylene meshes", *Hernia* 2001; 5:142-7.
Junge, K.. et al. "Functional and morphologic properties of a modified mesh for inguinal hernia repair", *World J Surg* 2002; 26:1472-80.
Scheidbach H, et al., "In vivo studies comparing the biocompatibility of various polypropylene meshes and their handling properties during endoscopic total extraperitoneal (TEP) patchplasty: an experimental study in pigs", *Surg Endosc* 2004; 18(2): 211-20.
Langenbech MR, et al., "Comparison of biomaterials in the early postoperative period", *Surg Endosc*. 2003; 17(7):1105-9.
O'Dwyer PJ, et al., "Randomized clinical trial assessing impact of a lightweight or heavyweight mesh on chronic pain after inguinal hernia repair", *Br J Surg*. 2005; 92(2):166-70.
Bracco P, et al., "Comparison of polypropylene and polyethylene terephthalate (Dacron) meshes for abdominal wall hernia repair: a chemical and morphological study", *Hernia* 2005, 9(1):51-55.
Hirano et al., "The blood biocompatibility of chitosan and N-acylchitosans", *J.Biomed.Mater.Res*. 1985, 19:413-417.
Malette et al., "Chitosan, a new hemostatic", *Ann. Th. Surg*. 1983, 36:55-58.
Muzzarelli et al., "Reconstruction of parodontal tissue with chitosan", *Biomaterials* 1989, 10:598-604.
Blondin C, et al., "Inhibition of complement activation by natural sulfated polysaccharides (fucans) from brown seaweed", *Molecular Immunol*. Mar. 1994; 31(4):247-53.

(Continued)

*Primary Examiner* — Michael G Hartley
*Assistant Examiner* — Lance Rider (57) ABSTRACT

A mesh implant is disclosed which may be utilized for treating urinary incontinence, hernias, uterovaginal prolapses and other related injuries.

15 Claims, 7 Drawing Sheets

(56) References Cited

OTHER PUBLICATIONS

Boisson-Vidal C, et al., "Neoangiogenesis induced by progenitor endothelial cells: effect of fucoidan from marine algae", *Cardiovascular & Hematological Agents in Medicinal Chem.* Jan. 2007; 5(1):67-77.

Ellouali M, et al., "Antitumor activity of low molecular weight fucans extracted from brown seaweed *Ascophyllum nodosum*", *Anticancer Res.* Nov.-Dec. 1993; 13(6A):2011-9.

Haneji K, et al., "Fucoidan extracted from Cladosiphon Okamuranus Tokida induces apoptosis of human T-cell leukemia virus type 1-infected T-cell lines and primary adult T-cell leukemia cells", *Nutrition and Cancer*, 2005; 52(2):189-201.

Haroun-Bouhedja F, et al., "In vitro effects of fucans on MDA-MB231 tumor cell adhesion and invasion", *Anticancer Res.* Jul.-Aug. 2002; 22(4):2285-92.

Logeart D, et al., "Fucans, sulfated polysaccharides extracted from brown seaweeds, inhibit vascular smooth muscle cell proliferation. II. Degradation and molecular weight effect," *Eur J Cell Biol.* Dec. 1997; 74(4):385-90.

Zvyagintseva TN, et al., "Inhibition of complement activation by water-soluble polysaccharides of some far-eastern brown seaweeds", *Comparative Biochem and Physiol* Jul. 2000; 126(3):209-15.

Klinge, et al., "Functional and Morphological Evaluation of a Low-Weight, Monofilament Polypropylene Mesh for Hernia Repair", *J. Biomed Mater Res* 2002 63:129-136.

Prokop, A., et al., "Water Soluble Polymers for Immunoisolation I: Complex Coacervation and Cytotoxicity", *Advances in Polymer Science*, 1998 136:1-51.

Rosen, M., et al., "Laparoscopic component separation in the single-stage treatment of infected abdominal wall prosthetic removal", *Hernia*, 2007 11:435-440.

\* cited by examiner

Figure 1 : Fucan leaching from Collagen-Fucan "Low Dose" films
*HPLC analysis on extracts after leaching in PBS buffer, 37°C*
( ' =minutes; h=hours; d=days)

Figure 2 : Bacterial adhesion on Collagen and Collagen-Fucan films (a): Adhesion of S. aureus on collagen (C) and collagen-fucan "Low Dose" (CF) films (b): Adhesion of S. aureus on PP (T'), collagen films (C') and collagen-fucan "Low Dose" films (CF') in presence of collagen-fucan "Low Dose" extracts Control: porous polypropylene

Figure 3: Fibroblast growth on collagen-fucan TH90 RED A2 0305 PUF 30

G0, G0.01, G0.05: Collagen film without textile containing respectively 0, 0.01 and 0.05% (m/V) of fucan T0, T0.01, T0.05: Composite Collagen Film/2D textile containing respectively 0, 0.01 and 0.05% (m/V) of fucan

FIG. 4

Figure 5: Chemotactic response of fucans on fibroblasts.

Figure 6: anti-complement activity of heparin H108, P240 RED and fucan TH90RED A2 0305 PUF 30 in solution.

Figure 7: Histological analysis of explanted composite implants

MESH IMPLANT

BACKGROUND

The present disclosure relates to medical implants. More particularly, the present disclosure relates to medical implants having a mesh configuration that are useful in tissue repair.

Implantable meshes may be inserted into a patient's body during a surgical procedure to reinforce, at least temporarily, deficient musculo-aponeurotic substrates. For example, implantable meshes may be utilized to treat hernias, urinary incontinence, uterovaginal prolapses, and other similar injuries.

Implanted meshes may be produced from non-absorbable or absorbable materials and may be constructed of monofilament threads or multifilament yarns. Some commercially available implantable meshes are made of monofilaments threads, the resulting mesh having relatively small pores, in some cases less than about 1 mm, and almost all are relatively rigid. This rigidity results in a mechanical mismatch between the implant and the host tissues which, in turn, may result in irritation of the tissue at the site of the implant. This irritation, combined with a lack of porosity, may lead to the formation of a pseudo fibrous capsule around the mesh implant which may cause discomfort, chronic pain, and increase the risk of recurrence.

Recently, some monofilament polypropylene meshes have been demonstrated to be oxidized in vivo when infection or acute inflammation occurs, resulting in some degradation of the material which could also be responsible for mesh stiffening, impaired abdominal wall movement when used to repair a hernia, and chronic pain.

Multifilament meshes are usually softer and more compliant than monofilament meshes. A multifilament mesh may possess a larger, more developed surface, which could be beneficial with respect to tissue integration, but could be detrimental with respect to increased bacterial contamination.

One way to attempt to minimize the risk of infection associated with the use of meshes in vivo is to apply antimicrobial coatings thereto. For example, U.S. Patent Application Publication No. 2005/0085924 and U.S. Pat. No. 5,217,493 both disclose meshes with coatings possessing antimicrobial agents. However, while these meshes may exhibit an antibacterial effect on a local and diffuse basis by inhibiting bacterial adhesion and proliferation as a result of the antibiotics and antiseptics included in the coatings, they may also damage the cytocompatibility of the material, thereby inhibiting and/or delaying the integration of the mesh with tissue. This inhibition or delay of the integration of the mesh material may generate adverse effects such as local necrosis, seroma, pseudocapsule formation, secondary infection, and the like.

Meshes with long term biocompatibility and infection resistance remain desirable.

SUMMARY

The present disclosure provides mesh implants which are tissue-friendly, with an initial rigidity providing easy handling and positioning of the mesh. In embodiments, the mesh implants may possess biological active agents capable of providing the mesh with desirable properties during the key phase of tissue integration, while maintaining for the long term a minimal amount of material possessing suitable mechanical properties. The strands of the mesh may include monofilament threads or multifilament yarns.

In embodiments, a suitable medical implant may include a mesh having strands and pores, with a coating on at least a portion of the mesh. The coating on the mesh, in embodiments, may include at least one collagen in combination with at least one polysaccharide which, in turn, may include fucans, dextrans, dextran derivatives, chitosan, cellulose, oxidized cellulose, polyglucuronic acid, hyaluronic acid and combinations thereof.

In other embodiments, a medical implant of the present disclosure may include a mesh having strands and pores and a coating on at least a portion of the mesh, wherein the coating includes at least one collagen in combination with at least one fucan.

In some embodiments, the strands of the mesh may include a synthetic non-absorbable material such as polyethylene, polypropylene, copolymers of polyethylene and polypropylene, blends of polyethylene and polypropylene, polyethylene terephthalate, polyamides, aramides, expanded polytetrafluoroethylene, polyurethane, polyvinylidene difluoride, polybutester, copper alloy, silver alloy, platinum, medical grade stainless steel, and combinations thereof.

Methods for forming such meshes and uses thereof are also provided.

BRIEF DESCRIPTION OF THE DRAWINGS

Various embodiments of the present disclosure will be described herein below with reference to the figures wherein.

DETAILED DESCRIPTION

According to the present disclosure there is provided a surgical mesh implant made of a biocompatible material. The mesh implants of the present disclosure may be suitable for soft tissue repair, for example when a permanent reinforcement is necessary. The implants of the present disclosure can also be used as an in-vitro support for biological evaluations, for example, cell cultures, microbiological assays, anti-complement and anticoagulant activity assays, and the like.

To support tissue ingrowth, it may be desirable to minimize the invasiveness of a mesh implant. At the same time, while it may be desirable for the implant to possess mechanical properties as close as possible to those of healthy tissue, the stiffer the mesh, the easier for the surgeon it is to handle the mesh, to spread it homogeneously on the defect, and adhere the mesh to the defect, thus decreasing the time required for a surgical procedure to repair a defect. Thus, a suitable mesh implant in accordance with the present disclosure may possess large pores, a limited amount of permanent, non-absorbable material, and isoelastic behavior. The mesh of the present disclosure may also, in embodiments, possess a coating which enhances its integration in vivo while at the same time minimizing bacterial colonization of the mesh. Such a coating may also, in embodiments, provide a stiffness to the mesh thereby facilitating its handling by a surgeon during implantation.

The mesh implant of the present disclosure may be made of strands which, in turn, may be made of filaments of any suitable biocompatible material. Suitable materials from which the mesh can be made should have the following characteristics: biocompatibility; sufficient tensile strength; sufficiently inert to avoid foreign body reactions when retained in the human body for long periods of time; exhibit minimal allergic and/or inflammatory response; non-carcinogenic; easily sterilized to prevent the introduction of infection when the mesh is implanted in the human body; minimal elasticity; minimal shrinkage; and easy handling characteristics for placement in the desired location in the body. Meshes of the present disclosure may be of monofilament or multi-filament in construction.

In some embodiments the filaments may be made of a plastic or similar synthetic non-absorbable material. Some examples of suitable non-absorbable materials which may be utilized include polyolefins, such as polyethylene, polypropylene, copolymers of polyethylene and polypropylene, and blends of polyethylene and polypropylene. Other non-absorbable materials which may be utilized include polyesters such as polyethylene terephthalate (PET), polyamides, aramides, expanded polytetrafluoroethylene, polyurethane, polyvinylidene difluoride (PVDF), polybutester, copper alloy, silver alloy, platinum, medical grade stainless steels such as 316L medical grade stainless steel, combinations thereof, and the like. Examples of commercially available polypropylene-based textile supports which may be utilized include those sold under the brand name PARIETENE® from Sofradim, and examples of commercially available PET-based textile supports which may be utilized include those sold under the brand name PARIETEX® from Sofradim.

In other embodiment the filaments of the mesh may be made of an absorbable material. Suitable absorbable materials include, but are not limited to, trimethylene carbonate, caprolactone, dioxanone, glycolic acid, lactic acid, glycolide, lactide, homopolymers thereof, copolymers thereof, and combinations thereof. Specific absorbable materials which may be suitable include, for example chitosan, cellulose, oxidized cellulose, combinations thereof, and the like.

In embodiments, the filaments described above may be utilized to form strands which, in turn, may be utilized to form a mesh implant of the present disclosure. For example, the strands may be warp knit or woven into a variety of different mesh shapes. Thus, the mesh may include strands, with pores formed between the strands. In some embodiments the strands may be arranged to form a net mesh which has isotropic or near isotropic tensile strength and elasticity.

The monofilaments utilized to produce the strands of the mesh implant may have a diameter of from about 0.07 mm to about 0.1 mm, in embodiments from about 0.08 mm to about 0.09 mm.

In embodiments, a mesh implant of the present disclosure may possess large hexagonal pores of more than about 1.5 mm in size, in embodiments from about 1.5 mm to about 4 mm in size. In some embodiments, the pores in a mesh implant in accordance with the present disclosure may be square in shape having dimensions of from about 1.2 mm to about 2.5 mm in size, in embodiments about 1.5 mm×1.5 mm in size.

A yarn in accordance with the present disclosure may possess a mass in grams per 10,000 meters (decitex or dtex) of from about 33 dtex to about 76 dtex, in embodiments from about 35 dtex to about 50 dtex.

As would be apparent to one of skill in the art, the surface density of a mesh can be decreased while maintaining its mechanical properties in an adequate range by selecting a monofilament thread having the right size and strength. For example, for a thread having the same diameter, a PET monofilament thread may have better mechanical properties compared to a polypropylene monofilament, so a smaller diameter PET monofilament thread can be used to obtain similar mechanical properties as the polypropylene monofilament, thus decreasing the amount of material implanted and enlarging pore sizes. Similarly, in other embodiments a PET monofilament thread having the same diameter as a polypropylene monofilament can be used with a more open textile structure to get similar mechanical properties as the polypropylene monofilament, thus decreasing the amount of material implanted and enlarging pore sizes. In both cases the surface density may not be lower because the PET specific weight is higher than the polypropylene specific weight. However, the developed surface will be lower and the pore size greater, thereby enhancing tissue ingrowth.

Moreover, for the same yarn count, a high tenacity polyester multifilament yarn may have better mechanical properties than a standard polyester multifilament yarn, so a thinner high tenacity polyester such as a high tenacity PET multifilament yarn could be used to obtain similar mechanical properties, thus decreasing the mesh surface density. A same count high tenacity PET multifilament yarn can be combined with a more open textile structure to get similar mechanical properties, thus decreasing the mesh surface density. In both cases the surface density will be lower, thereby limiting foreign body implantation and promoting mesh integration.

Mesh implants of the present disclosure may have a surface density of less than about 50 $g/m^2$, in embodiments from about 20 $g/m^2$ to about 50 $g/m^2$, in other embodiments from about 25 $g/m^2$ to about 35 $g/m^2$.

Mesh implants may also possess compliance and mechanical properties matching or very similar to native tissues, for example from about 10% to about 50% of elongation under a force of about 20 N of load in warp and weft direction, in embodiments from about 10% to about 40% of elongation under a force of about 20 N in warp direction and from about 20% to about 50% of elongation under a force of about 20 N in weft direction. Thus, in embodiments, a mesh of the disclosure may possess isoelastic behavior wherein the ratio of longitudinal elastic properties to transverse elastic properties is from about 0.7:1 to about 1.3:1, in embodiments of about 0.75:1 under a force of about 20 Newtons of load.

The pattern and the density of the strands forming the mesh provide the mesh implant with its necessary strength. Mesh implants in accordance with the present disclosure may possess a tensile strength of more than about 80 Newtons, in embodiments from about 80 Newtons to about 200 Newtons, in other embodiments from about 90 Newtons to about 150 Newtons, as determined according to ISO 13934-1 in both the warp and weft direction.

The shape of the mesh implant of the present disclosure may be varied depending upon the condition to be treated with the mesh implant. Mesh implants of the present disclosure may be circular, rectangular, trapezoidal, and the like. Due to the variability in patient morphology and anatomy, the implant may be of any suitable size. The mesh implant may have a width from about 50 mm to about 500 mm, in embodiments from about 75 mm to about 200 mm, and a length from about 50 mm to about 500 mm, in embodiments from about 90 mm to about 250 mm.

The thickness of the surgical mesh of the present disclosure may also vary, but may be less than about 5 mm. In some embodiments, the thickness of the mesh can be from about 0.05 mm to about 0.8 mm.

In embodiments a mesh may be formed utilizing a polyester monofilament, of a diameter of from about 0.07 mm to about 0.1 mm. In other embodiments, a multifilament polyester may be utilized to form a mesh, with a mass of about 49 dtex. In other embodiments, a multifilament high tenacity polyester, for example, a high tenacity PET, may be utilized to form a mesh, with a mass of about 49 dtex. In either embodiment, the mesh may have a low surface density of from about 20 $g/m^2$ to about 35 $g/m^2$.

Methods and apparatus suitable for forming meshes are within the purview of those skilled in the art. Suitable apparatus and methods include, for example, those disclosed in U.S. Pat. Nos. 6,408,656 and 6,478,727, the entire disclosures of each of which are incorporated by reference herein. In embodiments, a suitable mesh may be formed utilizing a tricot warp knitting machine or Rachel warp knitting machine with 2 or 3 guide bars. The gauge of needles utilized to form these meshes may be from about E22 to about E28 (i.e., about 22 to about 28 needles/inch), in embodiments from about E22 to about E24, in some embodiments about E24. In some embodiments, a mesh may be formed with two half threaded guide bars, being moved symmetrically for forming an open mesh according to the following graphics/bar movement.

In embodiments, to obtain pores with no specific shape and several pore sizes:
Guide-bar BI: 5.4/4.3/2.1/0.1/1.2/3.41//
Guide-bar BII: 0.1/1.2/3.4/5.4/4.3/2.1//
or
Guide-bar BI: 3.2/2.1/0.1//
Guide-bar BII: 0.1/1.2/3.2//

In some embodiments, a mesh may be formed with several guide bars using adequate threading diagrams and adequate bar movement to form an open mesh according to the following graphics.

In embodiments, to obtain single size square pores:
Guide-bar BI: 1.0/0.1//
Guide-bar BII: 6.6/0.0/2.2/0.0/6.6/4.4//
Guide-bar BIII: 0.0/6.6/4.4/6.6/0.0/2.2//

In other embodiments, to obtain single size hexagonal pores:
Guide-bar BI: 1.0/0.1/1.0/2.3/3.2/2.3//
Guide-bar BII: 0.0/1.1/0.0/3.3/2.2/3.3//

In embodiments, it may be desirable for a mesh to possess single size hexagonal pores, but any configuration of pores, or multiple pore configurations, may be utilized.

In order to facilitate handling by a surgeon during implantation, the meshes of the present disclosure may possess a coating thereon. Suitable coatings include, but are not limited to, collagens, chitosan, polyethylene glycol (PEG), polyglycolic acid (PGA), oxidized cellulose, polyarylates, polysiloxanes, combinations thereof, and the like.

In embodiments, a suitable coating may include collagen. The term "collagen" as used herein refers to all forms of collagen from any source including, but not limited to, collagen extracted from tissue or produced recombinantly, collagen analogues, collagen derivatives, modified collagens, and denatured collagens such as gelatin. For example, collagen may be extracted and purified from animal tissue including human or other mammalian sources, such as bovine or porcine corium and human placenta, or may be recombinantly or otherwise produced. The preparation of purified, substantially non-antigenic collagen in solution from animal sources such as bovine and porcine sources is within the purview of those skilled in the art. For example, collagen, including Type I collagen, may be extracted from pig dermis via an acid pH solubilization or via a pepsin digestion and purified with saline precipitations, utilizing processes within the purview of those skilled in the art. Moreover, U.S. Pat. No. 5,428,022 discloses methods of extracting and purifying collagen from the human placenta, and U.S. Pat. No. 5,667,839 discloses methods of producing recombinant human collagen in the milk of transgenic animals, including transgenic cows. Non-transgenic, recombinant collagen expression in yeast and other cell lines is described in U.S. Pat. Nos. 6,413,742, 6,428,978, and 6,653,450.

Collagen of any type, including, but not limited to, types I, II, III, IV, or any combination thereof, may be used in the coating of a mesh implant of the present disclosure. Either atelopeptide or telopeptide-containing collagen may be used; however, when collagen from a xenogenic source, such as bovine collagen or porcine collagen, is used, atelopeptide collagen may be suitable because of its reduced immunogenicity compared to telopeptide-containing collagen.

Collagen that has not been previously crosslinked by methods such as heat, irradiation, or chemical crosslinking agents may be utilized in some embodiments; in other embodiments previously crosslinked collagen may be used.

Collagens for use in coatings of mesh implants of the present disclosure may generally be in aqueous suspensions at a concentration of from about 20 mg/ml to about 120 mg/ml, in embodiments from about 30 mg/ml to about 90 mg/ml.

Collagen for use in forming a coating on a mesh implant of the present disclosure may be fibrillar or nonfibrillar. Collagens for use in the compositions of the present invention may start out in fibrillar form, then can be rendered nonfibrillar by the addition of one or more fiber disassembly agent(s). Where utilized, a fiber disassembly agent may be present in an amount sufficient to render the collagen substantially non-fibrillar at a pH of about 7. Suitable fiber disassembly agents include, without limitation, various biocompatible alcohols, amino acids, inorganic salts, and carbohydrates. Suitable biocompatible alcohols include glycerol and propylene glycol. Suitable amino acids include arginine. Suitable inorganic salts include sodium chloride and potassium chloride.

In embodiments, collagen type I and/or collagen type III, the main molecules of native extracellular matrix (ECM), may be utilized as the coating. Collagen types I and III are known to facilitate cellular adhesion, proliferation and differentiation.

The collagen coating leaves the pores empty for rapid colonization of the macrostructure of the mesh. Hence, the coating of the present disclosure should provide a better handling of the mesh and will also hide the main part of the surface of the synthetic yarns utilized to construct the mesh during the early integration phase.

In some embodiments, in addition to the collagen described above, a coating on a mesh implant of the present disclosure may also include additional absorbable materials. Such additional absorbable materials are within the purview of those skilled in the art and include, but are not limited to, trimethylene carbonate, caprolactone, dioxanone, glycolic acid, lactic acid, glycolide, lactide, polysaccharides including but not limited to, chitosan, polyglucuronic acid, hyaluronic acid, homopolymers thereof, copolymers thereof, and combinations thereof. When present, such absorbable materials may be present in a coating in an amount from about 20% to about 80% by weight of the coating, in embodiments from about 40% to about 60% by weight of the coating.

The coating of the present disclosure, in embodiments, may also include a bioactive molecule, such as a natural vegetal or synthetic polysaccharide. Suitable natural or synthetic polysaccharides include fucans, also called fucoidans, dextrans, dextran derivatives, cellulose, oxidized cellulose, chitosan, polyglucuronic acid, hyaluronic acid, combinations thereof, and the like.

In embodiments, a fucan may be utilized as the polysaccharide in the coating of a mesh implant of the present disclosure. As used herein, "fucan" includes any natural fucoidans, including those produced by recombinant techniques, as well as any fucoidan precursors, fucoidan derivatives or modified fucoidans and fucoidan derivatives, and depolymerized fucans. "Fucan" and "fucoidan" are used interchangeably herein. Sulfated fucans, also referred to simply as fucans, include natural sulfated polysaccharides extracted from the cell wall of brown algae, or the egg jelly coat of sea urchins, or from the body wall of sea cucumbers. Fucoidans are mainly absent from green algae (*Chlorophyceae*), red algae (*Rhodophyceae*), golden algae (*Xanthophyceae*) and from fresh water algae and terrestrial plants. In embodiments, suitable fucans may be extracted from brown algae. Suitable fucans include, for example, TH90RED A2 0305 PUF30 (extracted from *Ascophyllum Nodosum* brown algae) which is a low molecular weight fucan of about 17,000 g/mol with a polydispersity index of about 1.78.

Methods for extracting fucans from natural vegetal sources, including brown algae, are within the purview of those skilled in the art. Once obtained, the fucan may then be combined with collagen as described above to form a coating on a mesh implant of the present disclosure.

The addition of a fucan as part of a coating may permit quicker integration of the mesh in host tissue by enhancing fibroblastic and mesothelial cell proliferation and migration (respectively an increase of about 45% to 70% and about 50% to 80% of stimulation), inhibiting bacterial adhesion proliferation (about 20% to 40% of inhibition) and generating a favorable environment after implantation as evidenced by reduced anticomplement, limiting the immune response of the host, reducing anticoagulant activity, and enhancing the integration of the mesh without generating any adverse hemophilic effect. Biological properties of the fucans may be increased with a low molecular weight, low polydispersity index and a high sulfate rate.

A coating of the present disclosure may possess collagen in an amount from about 2% to about 5% by weight of the coating solution, in embodiments from about 2.5% to about 3.2% by weight of the coating solution, with a polysaccharide like a fucan present in the coating in an amount from about 0.001% to about 1% by weight of the coating solution, in embodiments from about 0.005% to about 0.05% by weight of the coating solution.

As noted above, in embodiments the collagen may be in a suspension. The polysaccharide described above may be added to this suspension which, in turn, may then be applied to a mesh implant. In other embodiments the collagen and polysaccharide may be placed into a solvent to form a solution, which may then be applied to a mesh. Any biocompatible solvent may be used to form such a solution. In embodiments, suitable solvents include, but are not limited to, methylene chloride, hexane, ethanol acetone, combinations thereof, and the like.

The coating may encapsulate an entire filament, strand or mesh. Alternatively, the coating may be applied to one or more sides of a filament, strand or mesh. Such a coating may improve the desired therapeutic characteristics of the mesh.

The coating may be applied to the mesh implant utilizing any suitable method known to those skilled in the art. Some examples include, but are not limited to, spraying, dipping, layering, calendaring, etc.

In some embodiments, the coating may add bulk to the mesh such that it is easier to handle. As the coating includes collagen and a polysaccharide, the coating should be released into the body after implantation and therefore should not contribute to the foreign body mass retained in the body. Thus, the advantages of a surgical implant having minimal mass may be retained.

The coating may be released into the body within a period of time from about 0 days to about 28 days following implantation, in embodiments from about 1 day to about 5 days following implantation.

As noted above, in embodiments a mesh implant in accordance with the present disclosure may possess initial handling properties which facilitate surgeon use, including use through a laparoscopic approach. Such handling properties may include, for example, initial memory, relative stiffness, surface smoothness, and combinations thereof.

Mesh implants of the present disclosure may also possess a tissue friendly surface capable of enhancing quick cellular adhesion, proliferation and connective tissue differentiation, while minimizing foreign body inflammation and decreasing the risk of bacterial adhesion and proliferation.

In embodiments, the mesh implant of the present disclosure may possess additional bioactive agents in its coatings. The term "bioactive agent", as used herein, is used in its broadest sense and includes any substance or mixture of substances that have clinical use. Consequently, bioactive agents may or may not have pharmacological activity per se, e.g., a dye. Alternatively, a bioactive agent could be any agent which provides a therapeutic or prophylactic effect; a compound that affects or participates in tissue growth, cell growth, and/or cell differentiation; a compound that may be able to invoke a biological action such as an immune response; or a compound that could play any other role in one or more biological processes.

Any agent which may produce therapeutic benefits, i.e., tissue repair, cell proliferation, limit the risk of sepsis, may be added in the coating formulation. Such agents include, for example, fucans, dextrans, dextran derivatives, carrageenan, alginate, hyaluronic acid, keratin sulfate, keratan sulfate, dermatan sulfate, chitin, chitosan, combinations thereof, and the like. For example, chitosan is biodegradable, has good biocompatibility, has been demonstrated to be hemostatic and bacteriostatic, and it also plays an important role in cell proliferation and tissue regeneration.

Examples of classes of bioactive agents which may be utilized in accordance with the present disclosure include antimicrobials, analgesics, antiadhesive agents, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the coating include quaternary ammonium, including triclosan also known as 2,4,4'-trichloro-2'-hydroxydiphenyl ether, diallyldimethylaminocarbonate (also known as DADMAC), chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the coating.

Other bioactive agents which may be included in the coating of a mesh implant of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as honnonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating of a mesh implant of the present disclosure include viruses and cells, peptides, polypeptides and proteins, analogs, muteins, and active fragments thereof, such as immunoglobulins, antibodies, beta glycans, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormnone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Any combination of bioactive agents may be utilized as part of a coating of the mesh implant of the present disclosure.

A coating may be applied to the mesh as a composition containing one or more bioactive agents, or bioactive agent(s) dispersed in a suitable biocompatible solvent.

Suitable solvents for particular bioactive agents are within the purview of those skilled in the art.

The rate of release of a bioactive agent from the coating on a mesh of the present disclosure can be controlled by any means within the purview of one skilled in the art. Some examples include, but are not limited to, the depth of the bioactive agent from the surface of the coating; the size of the bioactive agent; the hydrophilicty of the bioactive agent; and the strength of physical and physical-chemical interaction between the bioactive agent, the coating and/or the mesh material. By properly controlling some of these factors, a controlled release of a bioactive agent from the mesh of the present disclosure can be achieved.

In embodiments, filaments utilized to produce the strands of the mesh implant of the present disclosure may be made of bicomponent microfibers. Bicomponent microfibers typically include a core material and a surface material. In embodiments, the bicomponent microfibers may include a non-absorbable or long lasting absorbable core and a shorter lasting absorbable surface material. The surface material of the bicomponent microfiber may be absorbed by the body within a number of hours, such that only the core portion is left in the body for an extended period of time, typically for a long enough period of time to enable tissue ingrowth. Although a variety of materials may be used in forming these bicomponent microfibers, suitable materials include polypropylene for the core and polylactic acid or polyglycolic acid for the surface material. In another embodiment, the bicomponent microfibers may be made of a core material which may be rapidly absorbed by the body and a surface material which is not rapidly absorbed, but instead is absorbed for a longer period of time than the core.

In embodiments, the surface material of the bicomponent microfibers may provide the mesh implant with enhanced characteristics required for surgical handling. After insertion in the body, the surface material of the bicomponent microfiber may be absorbed by the body leaving behind the reduced mass of the core material as the strands of the mesh. For example, suitable bicomponent microfibers include a polypropylene non-absorbable portion as the core and a polylactic acid absorbable portion as the surface. The surface material is present during the surgical procedure when the mesh is being inserted and located in the patient, and provides the mesh with characteristics desirable for surgical handling. Following a period of insertion in the body, typically a few hours, the surface material is absorbed into the body leaving only the core material of the filaments in the body.

It may be desirable to provide a variety of implants having different sizes and dimensions so that a surgeon can select an implant of suitable size to treat a particular patient. This allows implants to be completely formed before delivery, ensuring that the smooth edge of the implant is properly formed under the control of the manufacturer. The surgeon would thus have a variety of differently sized and/or shaped implants to select the appropriate implant to use after assessment of the patient.

Methods of reducing fraying of the filaments to maintain a smooth edge of the mesh implant are within the purview of those skilled in the art and include, but are not limited to, heat treatment, laser treatment, combinations thereof, and the like. In some embodiments a heat treatment may be desirable, as such a treatment may promote adhesion of the strands forming the mesh, thereby facilitating removal of the mesh implant if required for any reason.

In another embodiment the mesh can be cut to any desired size. The cutting may be carried out by a surgeon or nurse under sterile conditions such that the surgeon need not have many differently sized implants on hand, but can simply cut a mesh to the desired size of the implant after assessment of the patient. In other words, the implant may be supplied in a large size and be capable of being cut to a smaller size, as desired.

Even where the cutting of the mesh causes an unfinished edge of the mesh to be produced, this unfinished mesh is not likely to cause the same problems as the rough and jagged edges of implants of the prior art, due to the coating, which protects the tissue from the mesh during the surgical procedure when damage to the tissue is most likely to occur.

Medical implants of the disclosure may include, but are not limited to, incontinence tapes and slings, and meshes, patches and/or implants for use in fascial repair, hernia repair, prolapse repair, and the like. Different shapes are suitable for repairing different defects. Thus, by providing a mesh implant which can be cut to a range of shapes, a wide range of defects, including those found in fascial tissue, can be treated.

In some embodiments, it may be desirable to secure the mesh in place once it has been suitably located in the patient. The mesh implant can be secured in any manner within the purview of those skilled in the art. Some examples include suturing the mesh to strong lateral tissue, gluing the mesh in place using a biocompatible glue, using a surgical fastener, or combinations thereof.

Any biocompatible glue within the purview of one skilled in the art may be used. In embodiments useful glues include fibrin glues, cyanoacrylate glues, combinations thereof, and the like. In other embodiments, the mesh implant of the present disclosure may be secured to tissue using a surgical fastener such as a surgical tack. Other surgical fasteners which may be used are within the purview of one skilled in the art, including staples, clips, helical fasteners, tissue anchors, suture anchors, bone anchors, hooks, combinations thereof, and the like.

Surgical fasteners useful with the mesh implant herein may be made from bioabsorbable materials, non-bioabsorbable materials, and combinations thereof. Examples of suitable absorbable materials which may be utilized to form a fastener include trimethylene carbonate, caprolactone, dioxanone, glycolic acid, lactic acid, glycolide, lactide, homopolymers thereof, copolymers thereof, and combinations thereof. Examples of non-absorbable materials which may be utilized to form a fastener include stainless steel, titanium, nickel, chrome alloys, and other biocompatible implantable metals. In embodiments, a shape memory alloy, such as nitinol, may be utilized as a fastener.

Surgical fasteners utilized with the mesh implant of the present disclosure may be made into any size or shape to enhance their use depending on the size, shape and type of tissue located at the repair site for attachment of the mesh implant. The surgical fasteners, e.g., tacks, may be used alone or in combination with other fastening methods described herein to secure the mesh to the repair site. For example, the mesh implant may be tacked and glued, sutured and tacked, or only tacked, into place.

The surgical fasteners may be attached to the mesh implant in various ways. In embodiments, the ends of the mesh may be directly attached to the fastener(s). In other embodiments, the mesh may be curled around the fastener(s) prior to implantation. In yet another embodiment, the fastener may be placed inside the outer edge of the mesh and implanted in a manner which pinches the mesh up against the fastener and into the site of the injury.

A mesh in accordance with the present disclosure possesses several desirable characteristics. In embodiments, where a non-absorbable material is utilized to form the strands of the mesh, the low surface density of a mesh of the present disclosure enhances the integration of the mesh with tissue, especially upon implantation in vivo. The collagen component of the coating minimizes the formation of adhesions and reduces the inflammation response to the mesh, while also improving the handling characteristics of the mesh for implantation by providing the mesh with stiffness. Moreover, the bioactive agent, in embodiments a fucan polysaccharide, may confer desirable properties to the mesh, for example the enhancement of cell proliferation and migration for enhanced and faster integration, antibacterial properties including the inhibition of both gram positive and gram negative bacteria, and the inhibition of inflammation, as evidenced by a decrease in complement activity. The bioactive agent, in embodiments a polysaccharide such as a fucoidan, may be released by the collagen coating immediately upon implantation, as well as for an extended period over several days.

A variety of different surgical approaches are contemplated herein for introducing the mesh implant of the present disclosure into a patient, including through an incision, laparoscopically, or through a natural approach such as, for example, vaginal approach, and the like.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLES

Example 1

A mesh was prepared with the following parameters. A high tenacity PET multifilament yarn, about 49 dtex was utilized to form the mesh. A tricot warp knitting machine utilizing gauge E24 needles (i.e., 24 needles/inch) was utilized. The mesh included hexagonal pores, which were formed using 2 guide-bars, with the following bar movement:

Guide-bar BI: 1.0/0.1/1.0/2.3/3.2/2.3//
Guide-bar BII: 0.0/1.1/0.0/3.3/2.2/3.3//

The resulting mesh had a low surface density of from about 20 $g/m^2$ to about 35 $g/m^2$, large pores of about 1.5 mm×1.5 mm, a ratio of longitudinal elastic properties/transversal elastic properties of from about 0.7:1 to about 1.3:1, and a breaking strength measured according to ISO 13934-1 in warp and weft direction of from about 80 Newtons to about 150 Newtons.

Example 2

The high tenacity PET mesh produced in Example 1 above was coated with a porcine collagen solution (about 0.8% m/V), which was a Type I collagen extracted from pig dermis. Dried collagen fibers were used, obtained after precipitation of an acid collagen solution and adjunction of NaCl, followed by washings and dryings of the resulting precipitate with acetone aqueous solution with concentrations of from about 80% up to about 100%.

The mesh was coated by immersion in the solution, followed by wringing and drying the textile under a laminar air flow. At the end of the enduction process, the collagen coating on the textile was reticulated by an aqueous solution of glutaraldehyde at about 0.5% m/V (Fluka, Glutaraldehyde about 25%), at pH about 6.5 to about 7.5, over a period of about 2 hours. A reduction with sodium borohydrate was then performed. The reagents in excess were washed several times with water and rinsed.

Example 3

The molecular weight, polydispersity and structure of the fucan TH90 RED A2 0305 PUF30, was physicochemically characterized via Gel Permeation Chromatography (GPC, on a Column Zorbax G-F450 associated with a column TSK G2000 SW XL), Infra Red analysis (FTIR, on a Perkin Elmer 1600) and elemental analysis. This fucan had a low molecular weight ($M_n$ about 12,000 to 17,000 g/mol), and a polydispersity index of about 1.78. The FTIR showed that the extraction process was reproducible and stable. Elemental analysis indicated that the sulfate content was about 25%. Furthermore, the final depyrogenation process utilized to obtain a pharmaceutical grade fucan did not alter the main molecule, as confirmed with GPC, FTIR and elemental analysis.

Example 4

In order to use the fucan with a mesh, the fucan of Example 3 was mixed with the collagen solution of Example 2 prior to application to the mesh of Example 1. Two concentrations of fucan were incorporated in the collagen solution: about 0.1% (m/V), sometimes referred to herein as "High Dose", and about 0.01% (m/V), sometimes referred to herein as "Low Dose". The coating of the yarns was performed as described above in Example 2.

In vitro assays were conducted in which about 1.5 mm diameter collagen-fucan disc shaped samples were prepared as models. The collagen-fucan films at a fucan concentration of about 0.1% contained about 250 μg of fucan, while the films at a fucan concentration of about 0.01% contained about 25 μg of fucan.

Fucan leaching from the collagen film was studied using High Pressure Liquid Chromatography (HPLC on a Dionex Carbo Pac 100).

Measurements were performed on the extracts of the collagen in combination with the collagen-fucan Low Dose after several hydration times of from about 20 minutes to about 96 hours in PBS buffer solution ($Na_2HPO_4$, $7H_2O$ at about 0.726 g/L, NaCl at about 9 g/L, $KH_2PO_4$ t about 0.21 g/L, [PBS Gibco, Invitrogen ref 20012-019] from Gibco, Life Sciences), at about 37° C. The results are set forth in FIG. 1.

Figure 1:
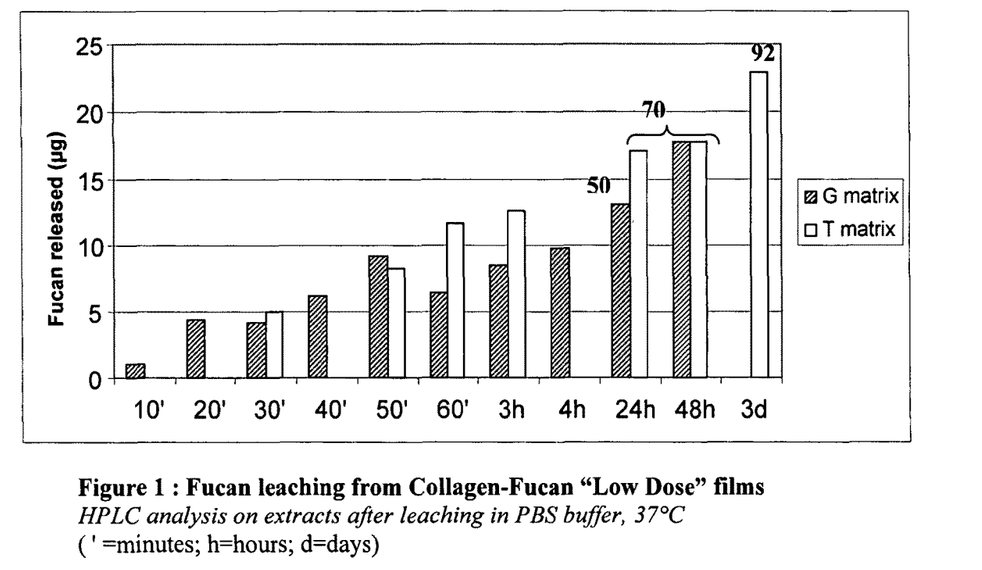
FIG. 1 is a graph of the results of HPLC analysis depicting the amount of fucan released from a collagen film in accordance with the present disclosure.

As can be seen in FIG. 1, about 50% and about 70% of the incorporated fucan was released during the first 24 and 48 hours, respectively, of hydration in the PBS medium.

From these results, it can be seen that the fucan on the mesh may possess both local and diffuse effects during the first phase of implantation, which is the critical phase, in terms of immune and adverse reaction due to the surgery.

Moreover, incorporation of the fucan in a collagen film did not significantly alter its physico-chemical properties, in the case of fucan concentrations of less than about 0.1% (m/V).

Example 5

A mediated bacterial adhesion assay involving the fucan in collagen as described above in Example 4 was conducted. Cultures of the bacterial strain *S. aureus* (ATCC 6538; Gram+) were prepared by incubating a well-isolated representative colony selected from an agar plate in about 1 ml of broth at about 37° C. overnight.

Bacteria were harvested from this saturated bacterial suspension by centrifugation at about 3500 revolutions per minute (rpm) for about 15 minutes. After discarding the supernatant, the bacterial pellet, about $10^7$ colony forming units (cfu)/ml, was suspended in about 1 ml of fresh broth and about 100 μL of tritiated thymidine (from Amersham, activity about 1 mCi/ml) was added. The resulting bacterial suspensions were incubated for about 3 hours at about 37° C. to obtain bacteria in the exponential growth phase. After the incubation period, the bacterial suspension was harvested twice at about 3500 rpm for about 15 minutes to remove the excess unbound radioactive thymidine.

A solution of PBS with $Ca^{++}$ and $Mg^{++}$ was then added to the bacterial pellet to obtain suitable bacterial dilutions (about $10^6$-$10^7$ cfu/ml) and the bacterial suspension was homogenized using a vortex-mixer.

Collagen from Example 2 and collagen-fucan Low Dose samples from Example 4 were utilized to prepare films. The films were first coated with plasma constituents and then incubated with about 500 μl of PBS for about 50 hours under stirring.

About 500 μl of the washed-log phase radiolabeled bacterial suspension (about $10^6$-$10^7$ cfu/ml) described above was then added to the films. The bacterial suspension on the film was incubated for about 3 hours at about 37° C. After about 5 washings with PBS buffer, each sample was transferred to counting vials; about 10 ml of scintillation fluid (Optiphase Hisafe, EG and G) were added; the amount of bacteria which adhered onto the implants was measured using an automatic β-liquid scintillation analyser model (Tri CARB 2100 TR (Packard IND 1401)).

In order to check that the investigated bacteriophobic activity was due to the fucan, additional collagen films (with and without fucan) were first coated with plasma constituents and incubated with a mixture of about 500 μl of the above washed-log phase radiolabeled bacterial suspension (about $10^6$-$10^7$ cfu/ml) in combination with about 500 μl of a solution of collagen-fucan Low Dose implant extracts obtained after about 50 hours of incubation in PBS buffer at about 37° C. The resulting mixture was incubated for about 3 hours at about 37° C. After about 5 washings with PBS buffer, each sample was transferred to counting vials; about 10 ml of scintillation fluid (Optiphase Hisafe, EG and G) were added; the amount of bacteria which adhered onto the implants was measured using an automatic β-liquid scintillation analyser model Tri CARB 2100 TR (Packard IND 1401).

Figure 2:
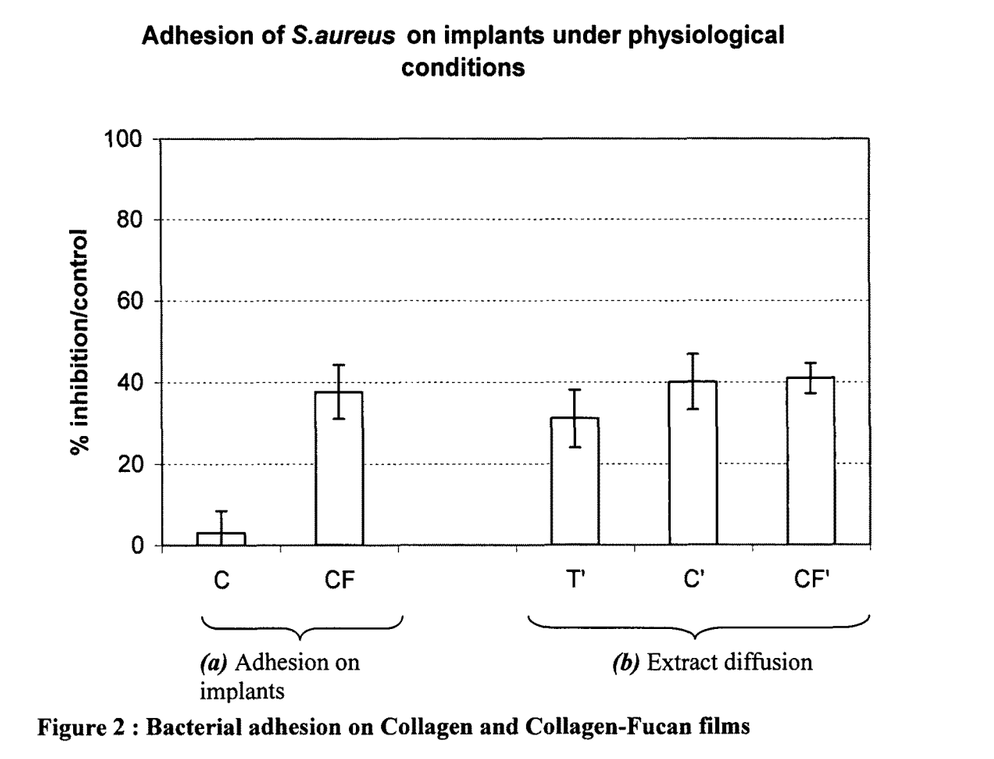
FIG. 2 is a graph depicting the adhesion of *S. aureus* on collagen and collagen-fucan films in accordance with the present disclosure (a), and adhesion of *S. aureus* on polypropylene (PP, T'), collagen films, and collagen-fucan films in the presence of an extract obtained from a collagen-fucan film in accordance with the present disclosure (b)

The results are set forth in FIG. 2, which shows the bacterial adhesion on collagen and collagen-fucan films. In FIG. 2, the two bar graphs for (a) demonstrate the adhesion of *S. aureus* on collagen (C) and collagen-fucan Low Dose (CF) films; the three bar graphs for (b) demonstrate the adhesion of *S. aureus* on a control of porous polypropylene (T'), collagen films (C') and collagen-fucan Low Dose films (CF') in the presence of collagen-fucan Low Dose extracts.

As can be seen in FIG. 2, the bacterial adhesion was more prevalent on the control and was statistically different than bacterial adhesion obtained on collagen films. Moreover, as can be seen in FIG. 2(*a*), films possessing fucan incorporated into collagen demonstrated a decrease in bacterial adhesion. The inhibition rate reached an average value of about 37% (after a period of incubation of about 50 hours in buffer).

In the case of the extract diffusion, an inhibition of bacterial adhesion on the three types of implants was observed (see FIG. 2(*b*)). Bacterial adhesion inhibition reached an average value of about 40%, which was nearly equal the rate obtained for the first experiment (about 37%). The bacterial inhibition obtained on T' (textile alone) was less (about 31% inhibition) as compared to the one observed on C' (collagen film) and CF' (Low Dose film).

The above results demonstrate that the fucan was released from the collagen-fucan Low Dose film during the first 50 hours, and was responsible for the inhibition of adhesion.

Example 6

In vivo experiments were conducted to check the antibacterial properties of a collagen-fucan implant in a rat contaminated model.

About 2.5×3.5 cm shaped composite implants were constructed with the two-dimensional non biodegradable textile of Example 1. Multiple implants were prepared; some possessed a collagen film coating as described in Example 2, while others possessed a collagen-fucan film coating as described in Example 4. The implants were implanted in rat peritoneal cavities at the site of a preformed 1.5×2.5 cm parietal defect. The implants were sutured with 6 points and the surgery was ended with suture strand. High virulence E. coli bacteria were inoculated ($10^9$ bacteria in 2 mL of phosphate buffer $Na_2HPO_4$, $7H_2O$; 0.1M; pH 7.2 [PBS, Invitrogen 20012-068]) by means of a percutaneous injection in the region of the implant/defect.

After time periods of about 2 days and about 30 days, the rats were sacrificed and the meshes explanted. The proliferated bacteria were detached from the explants and cultured on agar gelose before being counted. Immunohistology was also performed in order to identify the bacteria.

Fucan, at high dose, inhibited bacterial proliferation after 30 days (2 logs of inhibition). No significant effect was observed after 2 days of incubation. The results are summarized in Table 1 below.

TABLE 1

| # of Rats | Mesh reference | Timing | E. Coli |
|---|---|---|---|
| 7 | Textile* | J2 | 5.43E+08 |
| 7 | Textile High Dose** | J2 | 2.73E+08 |
| 7 | Textile Low Dose*** | J2 | 5.17E+08 |
| 7 | Textile* | J30 | 9.43E+10 |
| 7 | Textile High Dose** | J30 | 1.74E+09 |
| 5 | Textile Low Dose*** | J30 | 8.28E+10 |

J2 = rats sacrificed after 2 days
J30 = rats sacrificed after 30 days
*Textile - mesh with collagen coating
**Textile High Dose = mesh with collagen and High Dose fucan coating
***Textile Low Dose = mesh with collagen and collagen-fucan Low Dose coating Example 7

In-vitro cell culture characterization. The effects of fucans, incorporated in the collagen films as described above in Example 4, were analyzed at several concentrations on several different cells and their effects on cell proliferation were studied. The cells tested included fibroblasts, mesothelial cells, mesenchymal stem cells, urothelial cells, endothelial cells and smooth muscle cells (SMCs).

Normal human dermal fibroblasts (NHDF, Cambrex CC2511) were cultured in Dulbecco's Modified Eagle's Medium (DMEM, Cambrex CC3132) supplemented with about 10% fetal calf serum (FCS, Fischer 10270106), about 1% Fungizone (Fischer 15290026) and about 1% Penicillin/Streptomycin (Fischer 15140122). Cells were maintained in a controlled atmosphere (about 37° C., about 95% relative humidity and about 5% $CO_2$). All the experiments were carried out using cells with passage numbers of less than about 25 (passage=treatment with trypsin-ethylenediamine tetraacetic acid (EDTA)).

Figure 3:
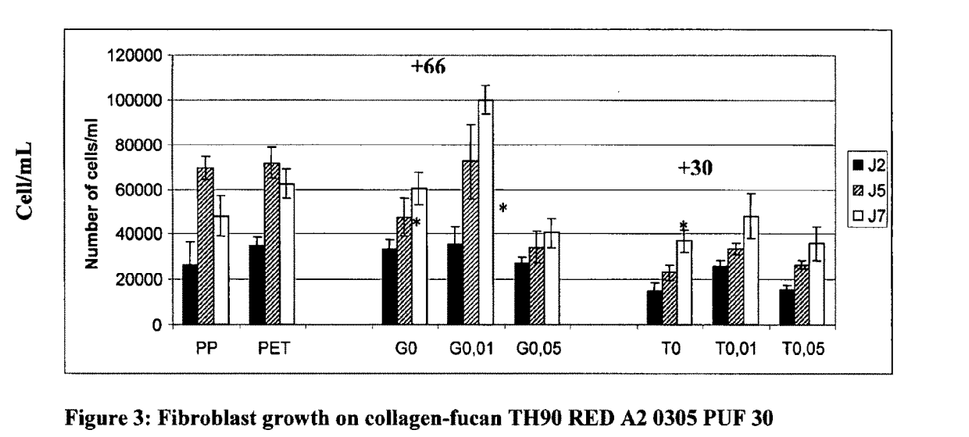
FIG. 3 is a graph depicting the growth of fibroblasts on polypropylene (PP), polyethylene terephthalate (PET), collagen films with varying concentrations of fucan, and collagen films with varying concentrations of fucan on a textile.

NHDF were grown onto the collagen-fucan film of Example 4, which included a collagen based gel associated with different concentrations of fucan, optionally associated with a 2D textile of Example 1. Cell growth was studied for about 7 days. Each experiment was repeated 3 times. The results of this experiment are set forth in FIG. 3, which shows the fibroblast growth on collagen-fucan TH90 RED A2 0305 PUF 30. As depicted in FIG. 3, G0, G0.01, G0.05 were collagen film without textile containing respectively about 0%, about 0.01%, and about 0.05% (m/V) of fucan; T0, T0.01, T0.05 were composite collagen films/2D textiles containing respectively about 0%, about 0.01%, and about 0.05% (m/V) of fucan.

The fibroblasts demonstrated an affinity for the collagen-fucan surfaces (see FIG. 3). The optimal concentration was evaluated at about 0.01% (m/V) of fucan in the collagen solution, i.e., a non degrading concentration for the physical integrity of the film.

The presence of the textile reduced the cell adhesion and proliferation rate. This may be due to the surface properties (e.g., planarity) induced by the presence of the textile, as well as differences in the degradation rate of the film and its impact on the cell adhesion and proliferation.

Example 8

Cell migration is a major process in tissue repair and wound healing. Cell migration was studied using a Boyden chamber assay through inserts with 8 µm pores. A depiction of a Boyden chamber is set forth in FIG. 4.

Figure 4:
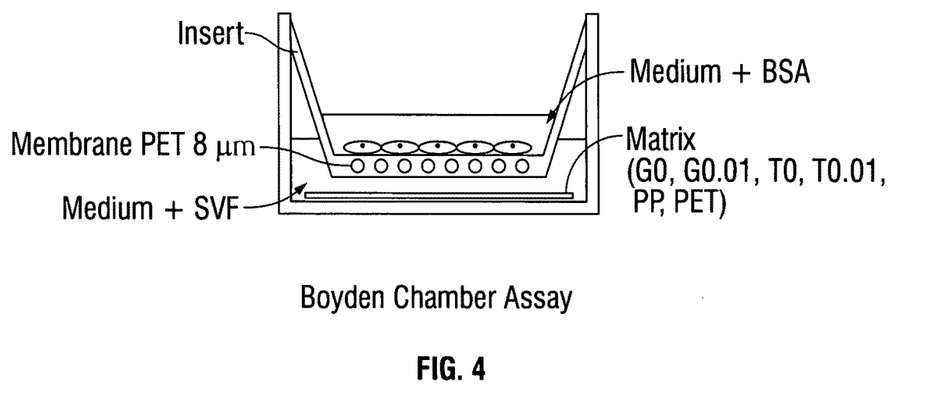
FIG. 4 is a depiction of a Boyden Chamber Assay utilized to test coated implants of the present disclosure.

Cells were suspended in culture medium and added to the upper chamber of the assay wells. Migration assays were performed in the presence of fucan matrices (T0, T0.01, G0, G0.01 as described above in Example 7), polypropylene (PP) or polyethylene terephthalate (PET) in the lower chamber. The chemotactic response to fucan was determined for fibroblasts. Positive controls were performed (migration in presence of about 20% fetal calf serum (FCS, Fischer 10270106)).

Figure 5:
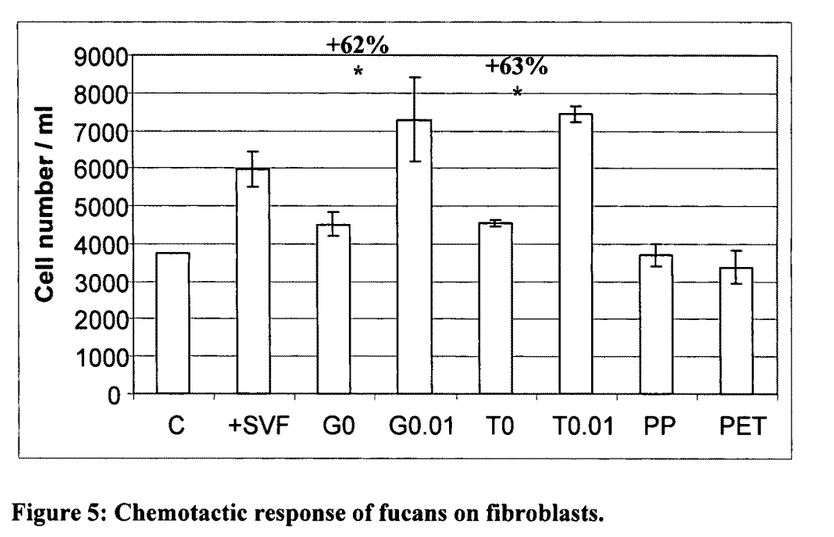
FIG. 5 is a graph depicting the chemotactic response of fucans on fibroblasts (varying concentrations of fucan in collagen films, with and without textile, with polypropylene and polyethylene terephthalate as a control)

The results are presented in FIG. 5, which demonstrates the chemotactic response of fucans on fibroblasts. As can be seen in FIG. 5, the migration of fibroblasts was stimulated in presence of fucans (comparison between G0.01 and G0 and between T0.01 and T0). The same effect was observed when fucan was released from the matrix including polypropylene and collagen (T0.01) or from the sole collagen matrix (G0.01), and reached about 60%.

No statistical difference was observed when the fibroblasts or mesothelial cells migrated in the presence of PP or PET matrices in the medium.

Example 9

The anti-complement activity of fucans was tested via a CH50 test, a standard hemolytic assay in total human serum.

Complement activation in human serum was induced by the introduction of sheep erythrocytes coated with rabbit antibodies and then recognized as foreign elements. This led to the activation of the classical pathway of the complement system, and hence to the lysis of erythrocytes.

The amount of released hemoglobin was then determined by an optical density (OD) measurement at about 414 nm. The human serum dilution was adjusted for a known amount of erythrocytes, in order to lyse about 50% of the red blood cells (CH50).

In order to check the impact of the fucan on the complement activation in solution, the fucan was added with the sheep erythrocytes. A decrease in cell lysis, as evidenced by a decrease of the OD at about 414 nm, demonstrated that the fucan inhibited the complement activation.

Heparin (heparin H108 173 UI/mg, Choay-Sanofi) and fucan P240 RED synthesized in the Laboratoire de Recherche sur les Macromolecules (LRM, CNRS UMR 7540, France) were also tested instead of fucan.

Figure 6:
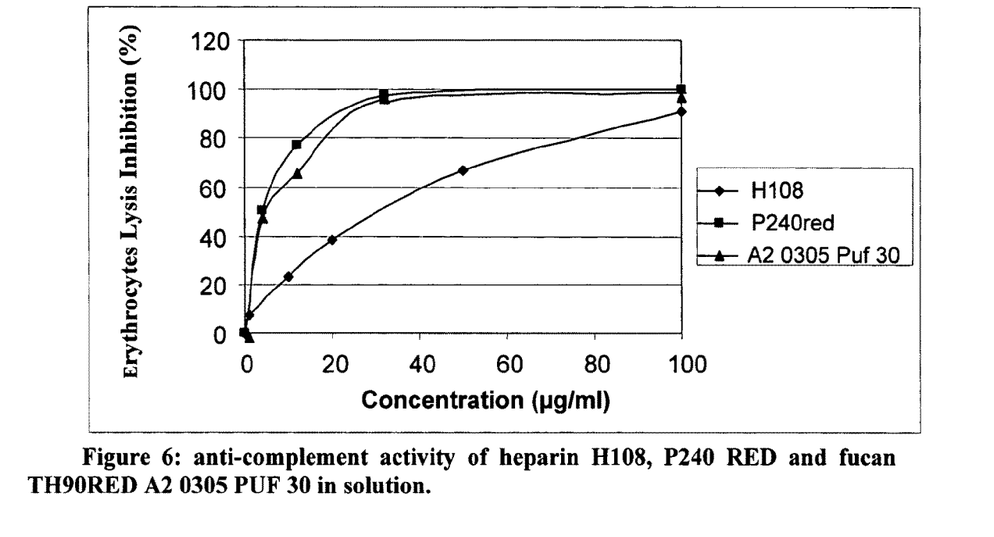
FIG. 6 is a graph depicting the anti-complement activity of heparin, fucan precursor P240 RED, and fucan TH90RED A2 0305 PUF 30 in solution.

The results are set forth in FIG. 6, which depicts the anti-complement activity of heparin H108, P240 RED and fucan TH90RED A2 0305 PUF 30 in solution.

As can be seen in FIG. 6, the fucan TH90RED A2 0305 PUF30 like its precursor P240 RED, presented dose-dependent anti-complement activity; both had an IC50 (median inhibition concentration) of about 4 µg/mL, evidencing a strong anti-complement activity as compared with the reference heparin H108 (IC50 about 30 µg/mL as measured in this test).

Example 10

In order to check the in-vivo integration of composite implants made of a 3D non biodegradable textile (PET) associated with a collagen film and collagen-fucan film, an intraperitoneal implantation in rat peritoneal cavity was performed. 2 sites in 25 rats were implanted with 3 kinds of implants: collagen/textile implant, as a control; collagen-fucan Low Dose/textile implant; and collagen-fucan High Dose/textile implant.

The mesh integration and associated adherences were observed after about 3 days, about 5 days, about 7 days, and about 6 weeks, by both macroscopic and immunohistological observations.

Figure 7:
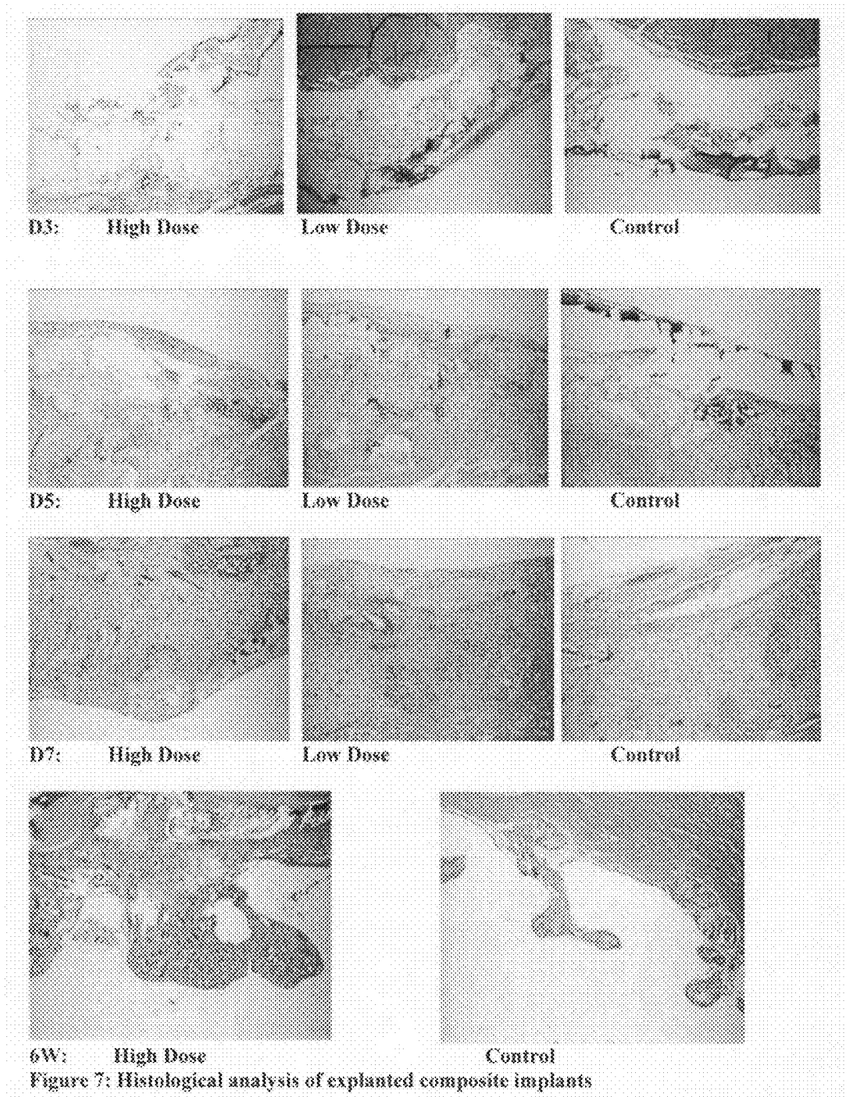
FIG. 7 are histological pictures obtained after intraperitoneal implantation of implants of the present disclosure in rats at various times after explantation.

The results of the histological analysis of explanted composite implants is set forth in FIG. 7 which depicts images of tissue obtained by histological observation. As can be seen in FIG. 7, after 3 days of implantation better integration of the mesh associated with the collagen-fucan Low Dose was observed compared with the composite control. The mesh containing the collagen-fucan Low Dose (0.01% (m/V)) showed multiple layers of fibroblastic cells after about 3 days of implantation. Statistical differences were observed for tissue integration between the collagen-fucan Low Dose and control.

The following days (see day 5 data and day 7 data on FIG. 7) presented a faster integration of the mesh associated with the collagen-fucan Low Dose compared to the composite control, with comparable inflammatory reactions. Integration of all the meshes was observed about 7 days after implantation. The moderate inflammatory reactions observed did not prevent the final integration of the mesh.

No data were available for the collagen-fucan Low Dose implant at 6 weeks, because the rat died during the experiment. This death was not due to the experiment.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A medical implant comprising:
a mesh comprising strands and pores; and
a coating on at least a portion of said mesh, the coating comprising at least one collagen in combination with at least one fucan, wherein the coating comprises a fucan concentration ranging from about 0.005% to about 0.5%.

2. The medical implant of claim 1, wherein strands comprise a synthetic non-absorbable material selected from the group consisting of polyethylene, polypropylene, copolymers of polyethylene and polypropylene, blends of polyethylene and polypropylene, polyethylene terephthalate, polyamides, aramides, expanded polytetrafluoroethylene, polyurethane, polyvinylidene difluoride, polybutester, copper alloy, silver alloy, platinum, medical grade stainless steel, and combinations thereof.

3. The medical implant of claim 1, wherein the strands comprise an absorbable material selected from the group consisting of trimethylene carbonate, caprolactone, dioxanone, glycolic acid, lactic acid, glycolide, lactide, chitosan, cellulose, oxidized cellulose, homopolymers thereof, copolymers thereof, and combinations thereof.

4. The medical implant of claim 1, wherein the collagen is selected from the group consisting of Type I collagen, Type III collagen, and combinations thereof, and the polysaccharide comprises a fucan.

5. The medical implant of claim 1, wherein the mesh strands comprise monofilament threads having a diameter of from about 0.07 mm to about 0.1 mm.

6. The medical implant of claim 5, wherein the pores have a size of from about 1.5 mm to about 4 mm.

7. The medical implant of claim 5, wherein the mesh has a surface density of from about 20 g/m$^2$ to about 50 g/m$^2$.

8. The medical implant of claim 1, wherein the mesh strands comprise multifilament yarns.

9. The medical implant of claim 8, wherein the multifilament yarn comprises a polyester selected from the group consisting of polyethylene terephthalate, high tenacity polyethylene terephthalate, and combinations thereof.

10. The medical implant of claim 8, wherein the pores have a size of from about 1.5 mm to about 4 mm.

11. The medical implant of claim 8, wherein the mesh has a surface density of from about 20 g/m$^2$ to about 50 g/m$^2$.

12. The medical implant of claim 8, wherein the multifilament yarn has a mass of from about 33 dtex to about 76 dtex.

13. The medical implant of claim 1, wherein the coating further comprises a bioactive agent selected from the group consisting of antimicrobials, analgesics, anti adhesive agents, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, narcotics, lipopolysaccharides, polysaccharides, polypeptides, proteins, hormones, enzymes, and combinations thereof.

14. The medical implant of claim 1, wherein the coating further comprises an absorbable material selected from the group consisting of trimethylene carbonate, caprolactone, dioxanone, glycolic acid, lactic acid, glycolide, lactide, homopolymers thereof, copolymers thereof, and combinations thereof.

15. The medical implant of claim 1, wherein the coating comprises a fucan concentration of about 0.01%.

* * * * *